(12) United States Patent
Chen et al.

(10) Patent No.: US 11,337,703 B2
(45) Date of Patent: May 24, 2022

(54) HANDLE ASSEMBLY AND STAPLER INCLUDING THE SAME

(71) Applicant: TOUCHSTONE INTERNATIONAL MEDICAL SCIENCE CO., LTD., Jiangsu (CN)

(72) Inventors: Zhi Chen, Jiangsu (CN); Yi Guo, Jiangsu (CN); Jiang Lin, Jiangsu (CN); Xiaowei Xu, Jiangsu (CN)

(73) Assignee: Touchstone International Medical Science Co., Ltd., Suzhou (CN)

( * ) Notice: Subject to any disclaimer, the term of this patent is extended or adjusted under 35 U.S.C. 154(b) by 159 days.

(21) Appl. No.: 16/957,544

(22) PCT Filed: Dec. 12, 2018

(86) PCT No.: PCT/CN2018/120699
§ 371 (c)(1),
(2) Date: Jun. 24, 2020

(87) PCT Pub. No.: WO2019/128721
PCT Pub. Date: Jul. 4, 2019

(65) Prior Publication Data
US 2020/0390445 A1 Dec. 17, 2020

(30) Foreign Application Priority Data

Dec. 26, 2017 (CN) .......................... 201721847008.7
Dec. 26, 2017 (CN) .......................... 201721849603.4

(51) Int. Cl.
*A61B 17/068* (2006.01)
*A61B 17/115* (2006.01)
(Continued)

(52) U.S. Cl.
CPC ... *A61B 17/1155* (2013.01); *A61B 2017/0042* (2013.01); *A61B 2017/00367* (2013.01);
(Continued)

(58) Field of Classification Search
CPC ...... A61B 17/1155; A61B 2017/00367; A61B 2017/2925
See application file for complete search history.

(56) References Cited

U.S. PATENT DOCUMENTS 4,351,466 A * 9/1982 Noiles .................. A61B 17/115
227/8
5,376,098 A 12/1994 Fontayne et al.
(Continued)

FOREIGN PATENT DOCUMENTS

CN 201098164 Y 8/2008
CN 100443059 C 12/2008
(Continued)

OTHER PUBLICATIONS

International Search Report regarding related PCT App. No. PCT/CN2018/122049; dated Mar. 6, 2019.
(Continued)

*Primary Examiner* — Eyamindae C Jallow
(74) *Attorney, Agent, or Firm* — Qinghong Xu

(57) ABSTRACT

A handle assembly and a stapler including the same are provided. The handle assembly includes: a first handle component and a second handle, a first end of which is rotatably connected with the first handle component. The handle can be divided into a first handle component and a second handle, and a linkage state of the first handle component and the second handle can be controlled by a moving position of a slider which can be returned by action of a compression spring after the slider is free from a force exerted by the indicator, and a position of the compression spring is defined by a first limiting structure of the slider and a second limiting structure of the first handle component.

19 Claims, 24 Drawing Sheets

(51) Int. Cl.
A61B 17/00 (2006.01)
A61B 17/072 (2006.01)
(52) U.S. Cl.
CPC .............. *A61B 2017/07257* (2013.01); *A61B 2017/07271* (2013.01); *A61B 2017/07285* (2013.01)

(56) References Cited

U.S. PATENT DOCUMENTS

| | | | |
|---|---|---|---|
| 6,050,472 A | 4/2000 | Shibata | |
| 7,658,311 B2* | 2/2010 | Boudreaux | A61B 17/07207 227/175.2 |
| 7,770,775 B2* | 8/2010 | Shelton, IV | A61B 34/76 227/178.1 |
| 9,445,810 B2* | 9/2016 | Cappola | A61B 17/068 |
| 9,549,738 B2* | 1/2017 | Mandakolathur Vasudevan | A61B 17/072 |
| 9,603,599 B2* | 3/2017 | Miller | A61B 17/115 |
| 2005/0103819 A1* | 5/2005 | Racenet | A61B 17/068 227/175.1 |
| 2014/0263548 A1* | 9/2014 | Tanner | A61B 17/1155 227/175.2 |

FOREIGN PATENT DOCUMENTS

| | | |
|---|---|---|
| CN | 105310747 A | 2/2016 |
| CN | 106388948 A | 2/2017 |
| CN | 206261635 U | 6/2017 |
| CN | 1969768 A | 8/2017 |
| CN | 106994034 A | 8/2017 |
| JP | 2009189831 A | 8/2009 |
| JP | 2015503949 A | 2/2015 |
| RU | 145252 U1 | 9/2014 |
| WO | 2010048811 A1 | 5/2010 |

OTHER PUBLICATIONS

Notice of Allowance regarding corresponding RU Pat. App. 2020122597/14; dated Nov. 13, 2020.
First Office Action regarding corresponding JP Pat. App. 2020-554351; dated Jun. 22, 2021.
Extended European Search Report regarding corresponding EP App. 18897538.7; dated Aug. 16, 2021.

* cited by examiner

HANDLE ASSEMBLY AND STAPLER INCLUDING THE SAME

CROSS-REFERENCE TO RELATED APPLICATIONS

This application is based upon PCT patent application No. PCT/CN2018/120699, filed on Dec. 12, 2018, which claims priority to Chinese Patent Application No. 201721849603.4 and No, 201721847008.7, filed on Dec. 26, 2017, the entire contents of which are incorporated herein by reference.

TECHNICAL FIELD

The present disclosure relates to medical instrument technology, more particularly, to stapler technology, and specifically to a handle assembly and a stapler including the same.

BACKGROUND

Digestive tract tumor is one of human diseases of high incidence. During treatment, a circular stapler is widely used for suturing physiological tissues such as tissues in the digestive tract, instead of the manual operation by doctors. The circular stapler is a common surgical instrument, and used for suturing from end to end, or from end to side of the physiological tissues of esophagus, stomach, intestine, etc., in a way of axial internal stapling. During the process of anastomoses, two sections of tissues are accommodated in the stapler, and form a circular anastomotic stoma after firing the stapler, to rebuild a tissue channel.

In the prior art, the circular stapler includes an instrument body, a handle assembly movably connected to the instrument body and an anvil assembly cooperated with the instrument body. The instrument body includes a cartridge assembly located on a distal end and a knob located on a proximal end thereof. The cartridge assembly includes a circular cartridge and a cutter, and the knob can be rotated relative to the instrument body. In the present disclosure, the positions of the distal end and the proximal end are defined relative to an operator, wherein, the proximal end is an end closer to the operator, the distal end is another end far from the operator and closer to a surgical position. The anvil assembly includes an anvil, an anvil cap on the top of the anvil, a cutter anvil inside the anvil and an anvil shaft detachably connected to the instrument body. During operation, after the tumor tissues are separated and removed, the anvil shaft is connected to the distal end of instrument body through a purse on one end of the tissues, the knob is rotated to shorten a distance between the cartridge and the anvil to an appropriate distance. The stapler is then able to be fired by pressing the handle to accomplish the suturing operation. Along with the development of medical instruments, the circular stapler has been more and more widely used for treatment of diseases such as hemorrhoids.

Meanwhile, in urinary surgical field, another kind of circular stapler is also applied to treat redundant prepuce and phimosis, which is called circumcision stapler. The structure of the circumcision stapler is similar to the circular stapler for digestive tract as aforementioned, except for the glans cap assembly cooperated with the instrument body. Similarly, the glans cap assembly includes an anvil, a glans cap fixedly connected to the anvil, a cutter anvil and a central rod detachably connected to the instrument body. During operation, the prepuce tissues to be cut are fixed to the glans cap, the central rod is configured to the distal end of the instrument body, and the knob is rotated to shorten a distance between the glans gap and the cartridge to an appropriate distance. The stapler is then able to be fired by pressing the handle to accomplish the suturing operation.

Along with the technological development, the firing transmission mechanism of the circular stapler has been improved with an insurance mechanism added. Therefore, when the stapler is not ready to be fired, even the doctor presses the handle, the handle cannot be moved for the lockout mechanism, to prevent the stapler from being fired by mistake. However, in practice, the lockout mechanism has some defects. For example, the lockout mechanism has some impacts on the operators' experience, and the casing of the stapler may be cracked if the doctor presses the handle vigorously.

SUMMARY

In the light of the problems in the prior art, the object of the present disclosure is to provide a handle assembly and a stapler including the same, to realize that, the handle can be divided into a first handle component and a second handle, and a linkage state of the first handle component and the second handle can be controlled by a moving position of a slider which can be returned by action of a compression spring after the slider is free from a force exerted by the indicator, and a position of the compression spring is defined by a first limiting structure of the slider and a second limiting structure of the first handle component.

In the present disclosure, a handle assembly to fire the stapler is provided, including:

a first handle component, provided with a slot including a first section and a second section connected with each other, in which slidably locate a slider, wherein, one end of the slider is provided with a first limiting structure, the end of the second section of the slot is provided with a second limiting structure, and a compression spring is located between the first limiting structure and the second limiting structure;

a second handle, a first end of which is rotatably connected with the first handle component;

wherein, when the slider is in the first section of the slot, and the first handle component is rotated in a first direction, the slider is not in contact with the second handle, therefore, the second handle is not rotated;

when the slider is moved to the second section of the slot by external force and the first handle component is rotated in the first direction, the compression spring becomes deformed, therefore, the slider is in contact with the second handle and actuates the second handle to rotate; when the slider is free from the external force, the restoring force of the compression spring actuates the slider to return.

In some embodiments, the handle assembly further includes an indicator, movable between a first position area and a second position area; wherein, when the indicator is moved from the first position area to the second position area, the slider is actuated to move from the first section to the second section of the slot.

In some embodiments, the slider includes two sliding portions and a contact portion in between; and the first handle component includes an inner cavity, the two side walls of which are respectively provided with one said slot; and the two sliding portions are located on the slots on the two side walls, respectively;

wherein, the end portion of the second sections of each slot is provided with one second limiting structure; one ends of each of sliding portion is provided with one first limiting structure, corresponding to each second limiting structure; and one compression spring is provided between each first limiting structure and the corresponding second limiting structure respectively provided with a said compression springs.

In some embodiments, the first handle component includes a first handle provided with the slot.

In some embodiments, the first handle component includes a first handle and a handle casing sleeved on outside of the first handle, wherein, the slot includes a first slot and a second slot connected with each other; the first slot includes the first section and the second section, and the second slot includes a first section and a second section corresponding to those of the first slot; the first slot is located on the first handle; and the second slot is located on the handle casing.

In some embodiments, one end of the slider is embedded in the second slot, and the second limiting structure is located at the end of the second section of the second slot.

In some embodiments, two sides of the first handle are respectively provided with two first slots, and the handle casing is correspondingly provided with two second slots, and the slider includes two sliding portions at two ends thereof and a contact portion in between; and each sliding portion is embedded in the corresponding second slot respectively;

wherein, the end portion of the second section of each second slot is provided with one second limiting structure, and one end of each sliding portion is provided with one first limiting structure, one compression spring is provided between each first limiting structure and the corresponding second limiting structure.

In some embodiments, a length of the sliding portion along an extension direction of the slot is greater than a length of the contact portion along the extension direction of the slot.

In some embodiments, the distal end of the handle casing is provided with the second slot which is connected with the upper surface of the handle casing.

In some embodiments, the first side of the distal end of the handle casing is in contact with the casing of the stapler, and the casing of the stapler is provided with a handle opening at a position corresponding to the second side of the distal end of the handle casing, for accommodating a distal end of the handle casing when being rotated in a first direction.

In some embodiments, the first limiting structure and the second limiting structure are convex columns, respectively, and two ends of the compression spring are respectively sleeved on the first limiting structure and the second limiting structure.

In some embodiments, a height of the second section of the slot is greater than that of the first section of the slot, and a smooth transition is made between the first section and the second section; an inner wall of the second section is provided with a support seat for a convex column; on which the second limiting structure, and a height of the support seat is greater than that of the second limiting structure.

In some embodiments, the first limiting structure and the second limiting structure are hanging hooks respectively, and the two ends of the compression spring are respectively hung on the first limiting structure and the second limiting structure.

In some embodiments, the handle assembly further includes:

a first pin, passing through the first handle component and the second handle, and fixed to the casing of the stapler; a first torsion spring, sleeved on the first pin, and the two ends of the first torsion spring being respectively in contact with the casing of the stapler and the second handle;

a second pin, fixed to the casing of the stapler; a second torsion spring, sleeved on the second pin, and the two ends of the second torsion spring being respectively in contact with the casing of the stapler and the first handle component.

In some embodiments, the handle assembly further includes:

a first pin, passing through the first handle component and the second handle, and fixed to the casing of the stapler; a first torsion spring, sleeved on the first pin, and the two ends of the first torsion spring being respectively in contact with the casing of the stapler and the second handle;

a compression spring, located between the first handle component and the casing of the stapler.

In some embodiments, the handle assembly further includes:

a first pin, passing through the first handle component and fixed to the second handle; a first torsion spring, sleeved on the first pin, and the two ends of the first torsion spring being respectively in contact with the first handle component and the second handle;

a second pin, passing through the second handle and fixed to the casing of the stapler; a second torsion spring, sleeved on the second pin, and the two ends of the second torsion spring being respectively in contact with the second handle and the casing of the stapler.

In some embodiments, the indicator is connected to a distal end of a pulling sheet, a proximal end of the pulling sheet is sleeved on a screw rod having a distal end connected to a knob, when the knob is rotated to pull the pulling sheet to move towards a proximal end of the stapler, the indicator is moved by the pulling sheet from the first position area to the second position area.

In the present disclosure, a stapler is provided including the handle assembly as aforementioned.

The handle assembly and the stapler including the same has the following advantages.

In the present disclosure, the handle assembly includes the first handle component and the second handle, the linkage state of which can be controlled by the moving position of the slider and only the rotation of the second handle can fire the stapler, so as to prevent the stapler from being fired by mistake when the stapler is not ready to be fired, and when in an invalid firing state, the first handle component can still be pressed and the casing of the stapler is prevented from being cracked; the compression spring is located between the slider and the slot, and the position of the compression spring is defined by a first limiting structure of the slider and a second limiting structure of the first handle component, therefore when the slider is free from the external force, the slider can be returned by the action of the compression spring.

BRIEF DESCRIPTION OF THE DRAWINGS

Embodiments of the present disclosure will now be described, by way of example only, with reference to the accompanying schematic drawings, and the other technical features, objects and advantages will be more obvious.

DETAILED DESCRIPTION

Figure 1:
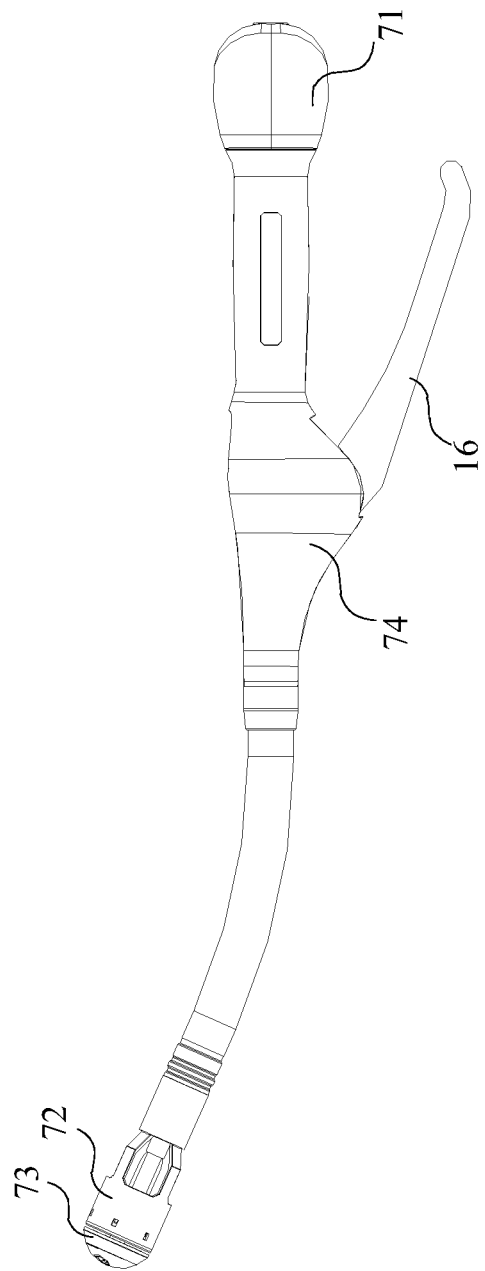
FIG. 1 is a schematic view of a handle assembly used in a stapler according to an embodiment of the present disclosure.
Figure 2:
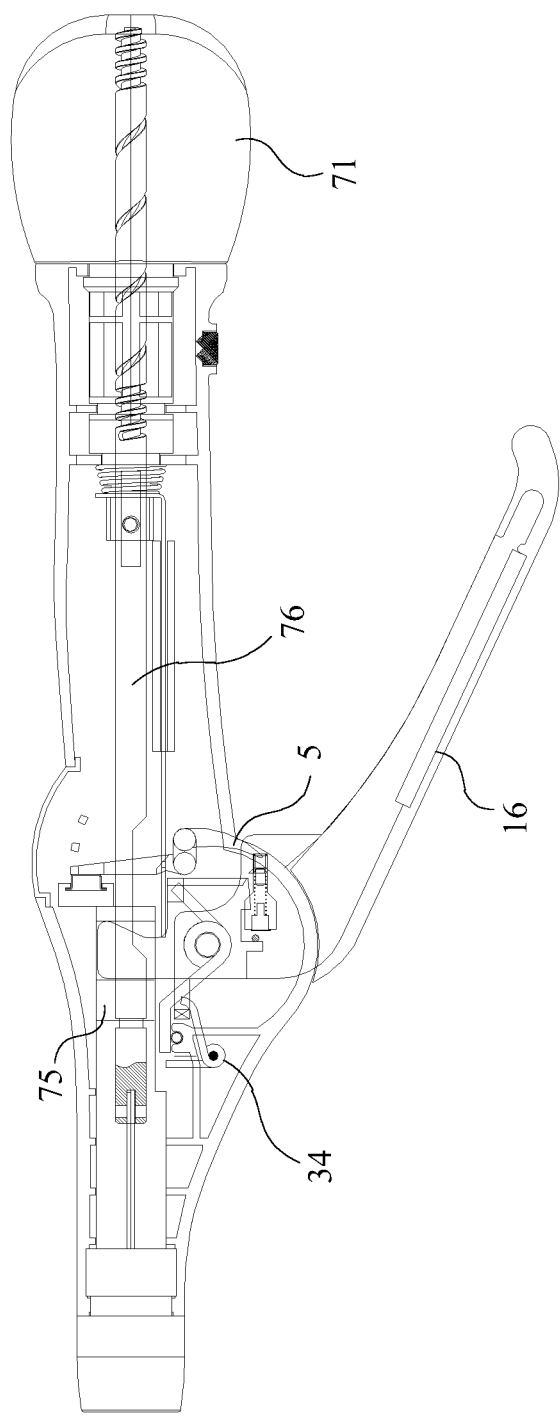
FIG. 2 is a schematic view of a handle assembly used in a conventional stapler according to a first embodiment of the present disclosure.
Figure 3:
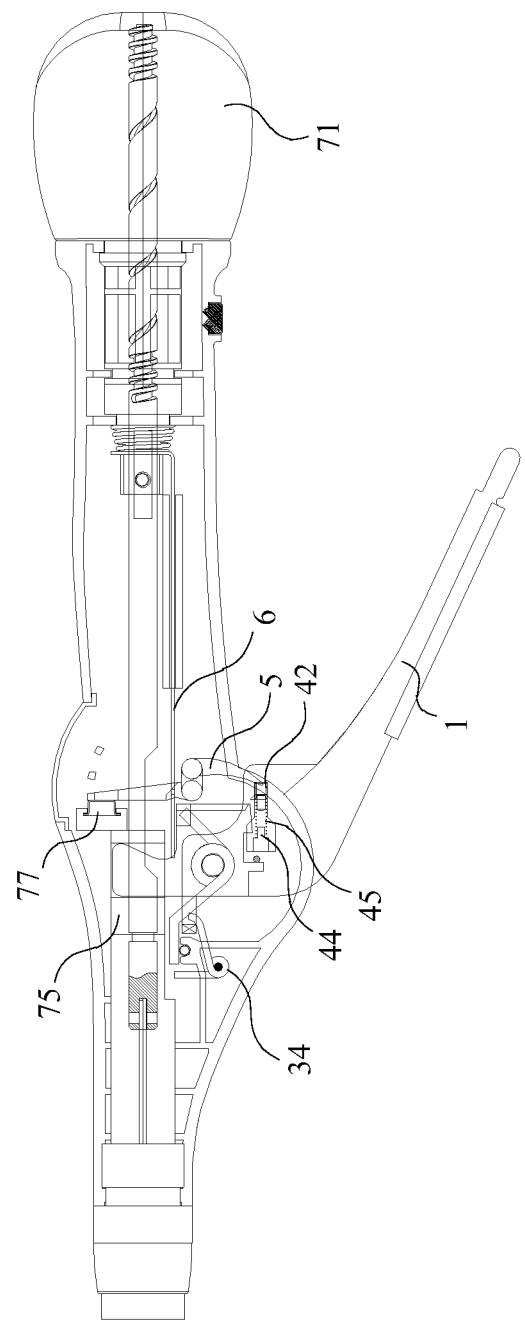
FIG. 3 is a schematic view of a handle assembly used in a conventional stapler according to a first embodiment of the present disclosure.

In the following, embodiments of the present disclosure will be described in detail with reference to the figures. The concept of the present disclosure can be implemented in a plurality of forms, and should not be understood to be limited to the embodiments described hereafter. In contrary, these embodiments are provided to make the present disclosure more comprehensive and understandable, and so the conception of the embodiments can be conveyed to those skilled in the art fully. Same reference signs in the figures refer to same or similar elements, so repeated description of them will be omitted.

In order to solve the problems in the prior art, the present disclosure provides a handle assembly used for firing of stapler. The handle includes a first handle component and a second handle, wherein, the first handle component is provided with a slot including a first section and a second section connected with each other. A slider is slidably located in the slot. One end of the slider is provided with a first limiting structure. An end portion of the second section of the slot is provided with a second limiting structure. A compression spring is located between the first limiting structure and the second limiting structure. A first end of the second handle is rotatably connected with the first handle component. The present disclosure further provides a circular stapler including the handle assembly.

When the slider is in the first section of the slot, and the first handle component is rotated in a first direction, the slider is not in contact with the second handle, therefore, the second handle is not rotated. When the slider moves to the second section of the slot by external force and the first handle component is rotated in the first direction, the compression spring becomes deformed, therefore, the slider is in contact with the second handle and actuates the second handle to rotate. When the slider is free from the external force, the restoring force of the compression spring actuates the slider to return to the first section of the slot.

Thus, the present disclosure prevents the stapler from being fired by mistake when the stapler is not ready to be fired, and when in an invalid firing state, the first handle component can still be pressed to move and a casing of the stapler is prevented from being cracked. The compression spring is located between the slider and the slot, and a position of the compression spring is defined by the first limiting structure of the slider and the second limiting structure of the first handle component, therefore when the slider is free from the external force, the slider can be returned by the action of the compression spring.

In the following, two embodiments of the present disclosure are respectively described combining the accompanying schematic drawings. FIGS. 1~15 show the structure of the stapler and its handle assembly according to a first embodiment of the present disclosure, wherein the first handle component includes a first handle, in a side wall of which located the slot. FIGS. 16~24 show the structure of the stapler and its handle assembly according to a second embodiment of the present disclosure, wherein, the first handle component includes a first handle and a handle casing sleeved on outside of the first handle, wherein, each of the first handle and the handle casing is provided with one slot. The slot on the first handle and the slot on the handle casing are connected with each other.

FIG. 1 shows the structure of a stapler according to an embodiment of the present disclosure. Wherein, a distal end of the stapler is provided with a cartridge assembly 72 and an anvil assembly; a proximal end of the stapler is provided with a knob and the handle assembly, outside of which is provided with a handle casing 16. The firing of the stapler can be achieved by pressing the handle assembly.

FIGS. 2~5 show the structure of the handle assembly in the initial state according to the first embodiment of the present disclosure, wherein part of the casing or part of the assembly is omitted for clear presentation of the structure of the handle assembly and its coordination with other parts. In order to achieve the above object, the handle assembly of the present disclosure is segmented. The handle assembly is divided into a first handle component and a second handle 2. The first handle component includes a first handle 1, and only the rotation of the second handle 2 can fire the stapler. The first handle 1 and the second handle 2 are rotatably connected. When the first handle 1 and the second handle 2 are not linked together, the operator can press the first handle 1, but can neither actuate the second handle 2 to rotate, nor fire the stapler. When the first handle 1 and the second handle 2 are linked together, the operator can press the first handle 1 to actuate the second handle 2 to rotate, thus firing the staple.

For controlling the linkage state of the first handle 1 and the second handle 2, the first handle 1 is further provided with a first slot 41 including a first section 411 and a second section 412 connected with each other, and a slider 42; the second handle 2 includes a handle contact portion. When the slider 42 is in the first section 411 of the first slot 41, and the first handle 1 pressed is rotated in a first direction, the slider 42 is not in contact with the handle contact portion, therefore, the second handle 2 is in an insurance position. That is to say, despite the rotation of the first handle 1, the stapler will not be fired, and the stapler is in the invalid firing state. In this embodiment, the first direction is an anticlockwise direction as shown in the FIGS., however, the present disclosure is not limited to it. Thus, the first handle 1 can be rotated easily when pressed by the doctor, while the second handle 2 will not be actuated. Therefore, the stapler is in the invalid firing state, and the first handle 1 can be rotated by a very small force. The doctor can also know the stapler is in the invalid firing state through his operation experience and the casing of the stapler will not be cracked.

When the slider 42 is in the second section 412 of the first slot 41, and the first handle 1 is pressed to be rotated in the first direction, the slider 42 is in contact with the handle contact portion and actuates the second handle 2 to be rotated from the insurance position to a firing position. When the second handle 2 is rotated anticlockwise, the second handle 2 can actuate a staple pushing rod 75 to move to the distal end of the stapler, to fire the stapler.

It should be noted that, the first section 411 and the second section 412 of the first slot 41 as described in the present disclosure are relative concepts, not necessarily indicate two ends of the first slot 41. That is to say, in the perspective shown in FIG. 5, the first section 411 of the first slot 41 can be located on a right side of the second section 412. The relationship between the slider 42 and the handle contact portion 25, when the first handle 1 is pressed while the slider 42 in the first section 411 of the first slot 41 and when the first handle 1 is pressed while the slider 42 in the second section 421 of the first slot 41, is different. When the slider 42 is in the first section 411 of the first slot 41, the slider 42 will not be in contact with the handle contact portion; when the slider 42 is in the second section 421 of the first slot 41, the slider 42 will be in contact with the handle contact portion.

In the embodiment, the movement of the slider 42 from the first section 411 to the second section 421 of the first slot 41 is controlled by an indicator 5. The indicator 5 includes a first end 51, a fixed portion 53 and a second end 42. The first end 51 of the indicator 5 is provided with a convex portion 54, positioned correspondingly to a position of a pulling hook of a pulling sheet 6. The fixed portion 53 of the indicator 5 is rotatably fixed to the casing 74 of the stapler. The tail of the pulling sheet 6 is fixed to a screw rod 76 to move along with the screw rod 76. When the knob 71 is rotated in a direction, the screw rod 76 will move toward the proximal end of the stapler to actuate the pulling sheet 6 to move toward the proximal end of the stapler. The pulling sheet 6 can actuate the first end 51 of the indicator 5 to be rotated in a second direction, so that the first end 51 of the indicator 5 moves from a first position area to a second position area. Thus, the second end 52 of the indicator 5 actuates the slider 42 to move from the first section 411 to the second section 412 of the first slot 41. In this embodiment, the second direction is a clockwise direction as shown in the FIGS., however, the present disclosure is not limited to it. Wherein, a window is provided on the instrument body, between the first position area and the second position area, through which the position of the first end 51 of the indicator can be observed during operation. When the first end 51 of the indicator is in the first position area, the stapler is in an insurance state and not ready to be fired. When the first end 51 of the indicator is in the second position area, the stapler is ready to be fired. To give a more obvious indication to the doctor, the window corresponding to the second position area indicating the stapler being ready to be fired is colored green, which is already existed in the prior art.

For achieving the return of the slider 42 after the slider 42 is free from the force exerted by the indicator 5, the slider 42 is further provided with a compression spring 45. Specifically, one end of the slider 42 is provided with a first limiting structure 43; the end portion of the second section 412 of the first slot 41 is provided with a second limiting structure 44. The compression spring 45 is located between the first limiting structure 43 and the second limiting structure 44. The end portion of the second section 412 of the first slot 41 is the end of the second section 412 far from the first section 411, that is the left position in FIG. 5 herein. When the first end 51 of the indicator 5 moves from the first position area to the second position area, the second end 52 of the indicator 5 actuates the slider 42 to move from the first section 412 to the second section 412 of the first slot 41, compressing the compression spring 45 to become deformed. When the external force is released, the first end 51 of the indicator 5 can return to the first position area, the second end 52 of the indicator 5 is not in contact with the slider 42, therefore, the restoring force of the compression spring 45 can push the slider 42 to return to the first section 411 of the first slot 41.

Further, in this embodiment, the first handle includes a cavity 13, two side walls of which are respectively provided with two first slots 41. The slider 42 includes two sliding portions 421 and a contact portion 422 between the two sliding portions 421. The two sliding portions 421 are movably located on the first slot 41. Two second limiting structures 44 are provided on the end portions of the second sections 412 of the two first slots 41, respectively. Two first limiting structures 43, corresponding to the two second limiting structures 44, are provided on the ends of the two sliding portions, respectively. One compression spring 45 is provided between each first limiting structure 43 and the corresponding second limiting structure 44, respectively. A length of the sliding portion 421 along an extension direction of the first slot 41 is greater than a length of the contact portion 422 along the extension direction of the first slot 41, to maintain the stability of the slider 42 in the first slot 41.

In this embodiment, the first slot 41 connects inside and outside of the cavity 13 of the first handle 1. That is, the structure of the first slot 41 and the slider 42 can be seen from an outer wall of the first handle 1. The compression spring 45 can be directly installed outside the first handle 1, and a current position of the slider 42 and a compressed state of the compression spring 45 can be seen from the outside of the first handle 1. In this embodiment, the first handle 1 is further provided with a handle casing 16 sleeved on the outside of the first handle 1. The handle casing 16 is generally made of plastic material, used to protect the first handle 1, and has smooth lines to improve the user experience.

In this embodiment, the first limiting structure 43 and the second limiting structure 44 are convex columns, respectively, and two ends of the compression spring 45 are sleeved on the first limiting structure 43 and the second limiting structure 44 respectively. Therefore, sizes of the two convex columns are adapted to sizes of the compression spring 45 to avoid the separation of the compression spring 45 from the convex columns. In practical applications, the structure of the limiting structure of the compression spring 45 is not limited to this, and other structures are also within the protection scope of the present disclosure. For example, the first limiting structure 43 and the second limiting structure 44 may be hanging hooks, respectively, and two ends of the compression spring 45 are respectively hung on the first limiting structure 43 and the second limiting structure 44 to limit the compression spring 45.

In this embodiment, a first pin 31 passes through the first handle 1 and the second handle 2 at the same time, the first pin 31 is fixed to the casing 74 of the stapler, and the first torsion spring 32 is sleeved on the first pin 31. Two ends of the first torsion spring 32 are respectively in contact with the casing 74 of the stapler and the second handle 2. After the second handle 2 rotates, if the external force is released, the second handle 2 can return.

Since both the first handle 1 and the second handle 2 rotate around the first pin 31, the centers of rotation of the first handle 1 and the second handle 2 are unified, and the operator's experience is better. In addition, in this embodiment, a second torsion spring 34 and a second pin 33 are also provided for the return of the first handle 1. The second pin 33 is fixed to the casing 74 of the stapler, the second torsion spring 34 is sleeved on the second pin 33, and the two ends of the second torsion spring 34 are respectively in contact with the casing 74 of the stapler and the first handle 1.

Only one connection method of the first handle 1 and the second handle 2 is given here, however, the present disclosure is not limited to this, and the two handles may be connected in other ways, which are within the protection scope of the present disclosure. For example, the second torsion spring and the second pin for the return of the first handle can be replaced with at least one compression spring. The compression spring is connected between the first handle and the casing of the stapler. When the first handle rotates, the compression spring becomes deformed, when the first handle is released, the compression spring is restored and the first handle returns. Further, a structure having dual rotation center may be adopted. For example, in a structure having dual rotation center, the handle assembly is also provided with a first torsion spring, a first pin, a second torsion spring and a second pin shaft. The first pin is fixed to the second handle, and passes through the first handle, the first torsion spring is sleeved on the first pin, and the two ends of the first torsion spring are respectively in contact with the first handle and the second handle, which can realize the return of the first handle; the second pin is fixed to the casing of the stapler and passes through the second handle, the second torsion spring is sleeved on the second pin, and two ends of the second torsion spring are respectively in contact with the second handle and the casing of the stapler to realize the return of the second handle. The first handle and the second handle rotate around the first torsion spring and the second torsion spring, respectively.

Figure 4:
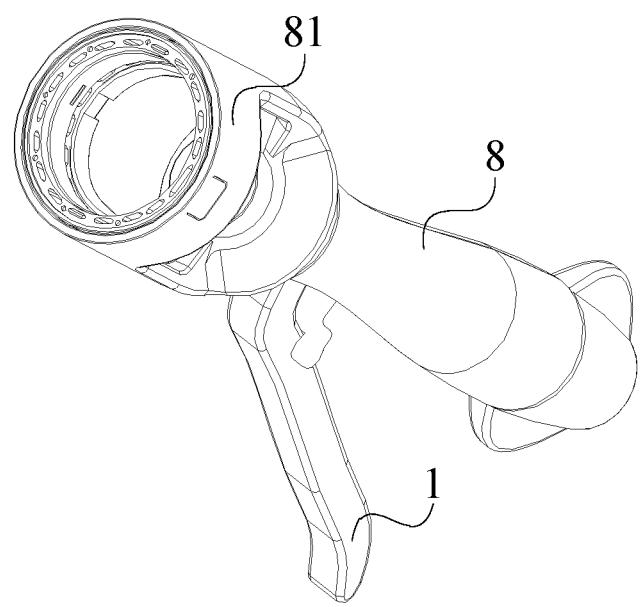
FIG. 4 is a schematic view of the handle assembly used in a circumcision stapler according to the first embodiment of the present disclosure.
Figure 5:
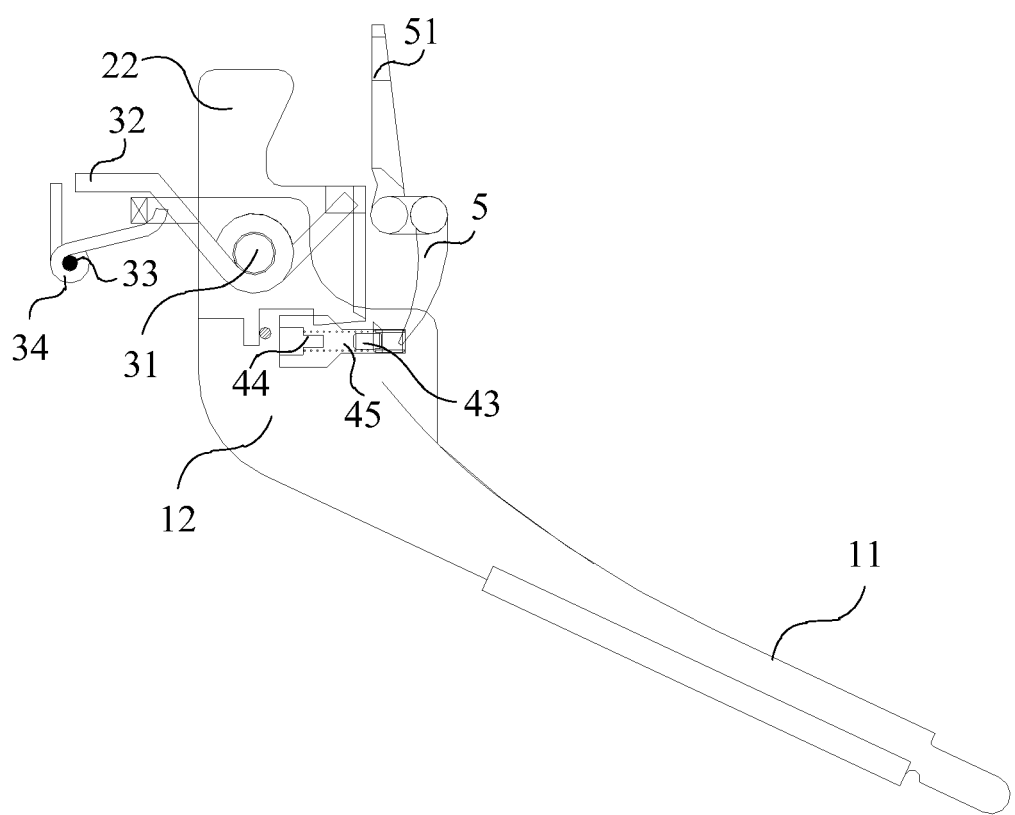
FIG. 5 is a schematic view of the handle assembly in an initial state according to the first embodiment of the present disclosure.

The handle assembly of the present disclosure can be applied not only to the conventional circular stapler, but also to a circumcision stapler. For example, as shown in FIG. 4, the structure of the instrument body 8 of the circumcision stapler to which the handle assembly is applied is shown. The distal end of the instrument body 8 of the circumcision stapler includes a cartridge assembly 81, and a glans cap assembly (not shown in the figures) cooperated with the cartridge assembly 81 is also provided. When using a circumcision stapler, the second handle 2 is movably connected to one end of the circumcision stapler. The second end of the second handle 2 is cooperated with a staple pushing component of the circumcision stapler. When the stapler is ready to be fired, the staple pushing component is pushed by the second handle 2 to fire the circumcision stapler.

Figure 6:
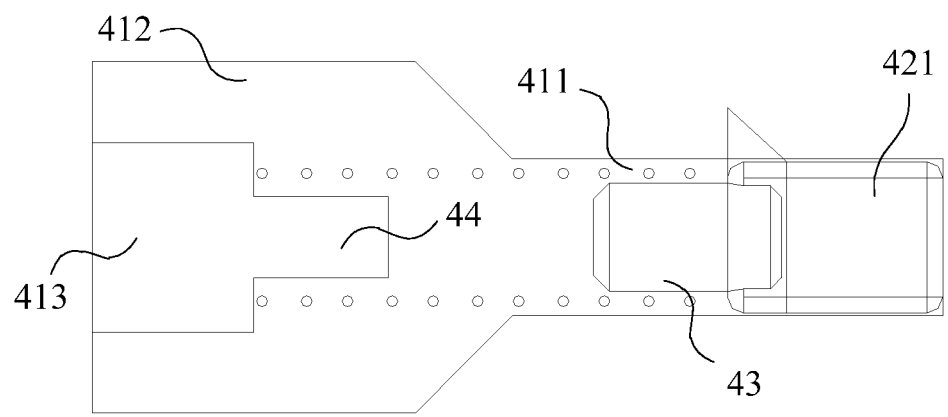
FIG. 6 is a schematic view of a slot according to the first embodiment of the present disclosure.
Figure 7:
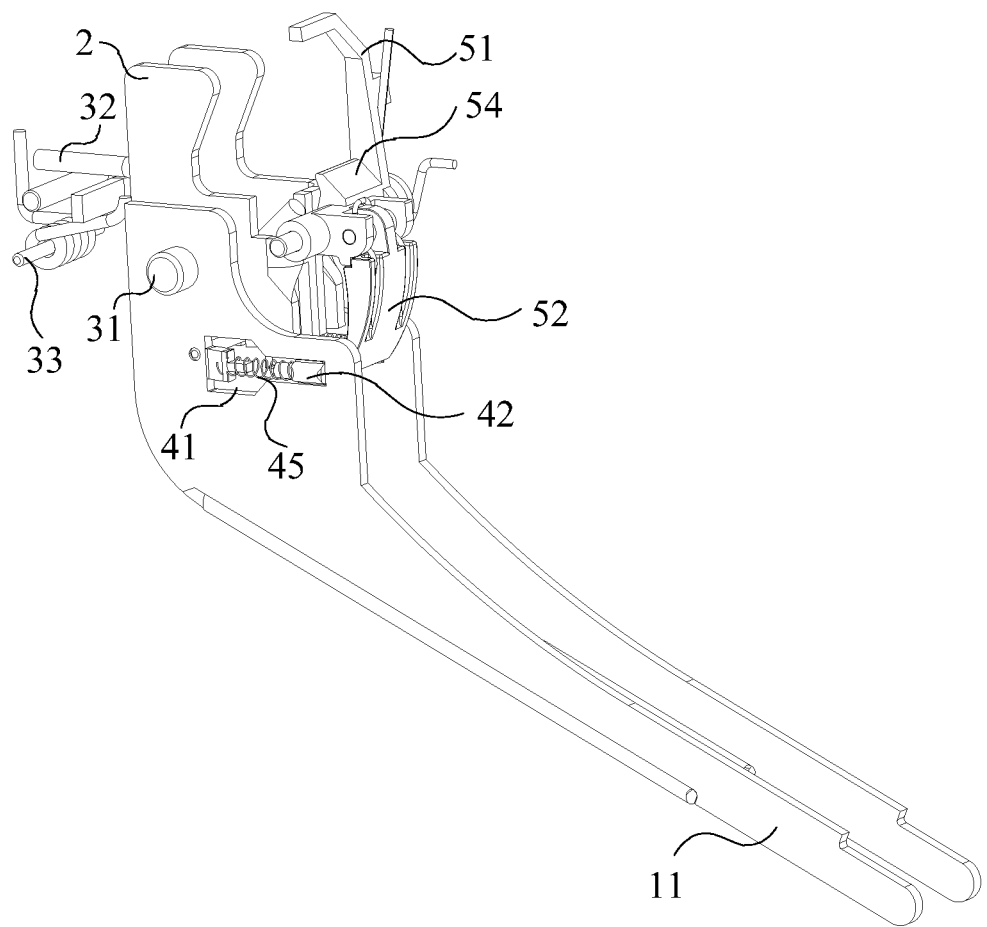
FIG. 7 is a stereoscopic view of the handle assembly in the initial state according to the first embodiment of the present disclosure.
Figure 8:
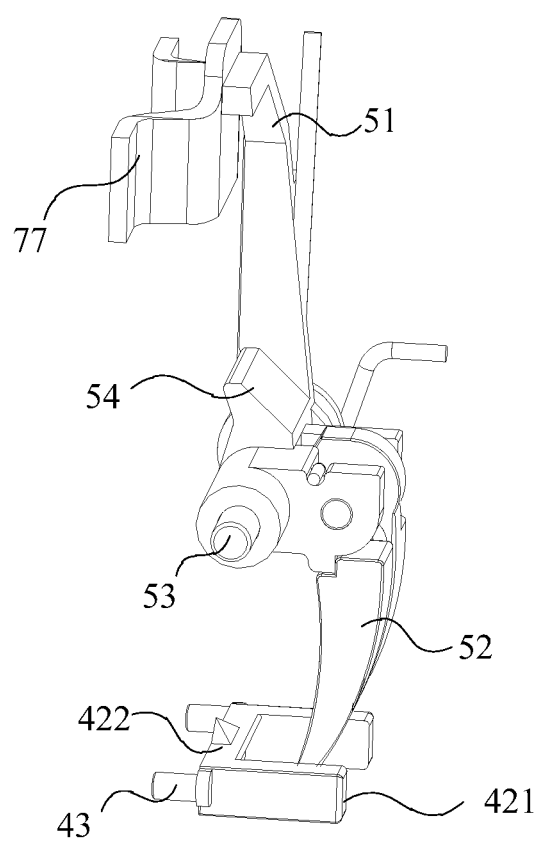
FIG. 8 is a stereoscopic view of an indicator and a slider in the initial state according to the first embodiment of the present disclosure.

The structure of the first slot 41 in this embodiment can be seen in FIGS. 6-8. Wherein, a height of the second section 412 of the first slot 41 is greater than a height of the first section 411, and the first section 411 and the second section 412 smoothly transit through an inclined plane. Inner wall of the end of the second section 412 is provided with a support seat 413 for a convex column; the second limiting structure 44 is located on the convex pillar support seat 413, and a height of the support seat 413 is greater than a height of the second limiting structure 44. Since the height of the second limiting structure 44 itself is limited by the compression spring 45, if it is made very large, it cannot be connected to the compression spring. Therefore, in this embodiment a convex pillar support seat 413 is added to provide better support to the second limiting structure 44.

Figure 9:
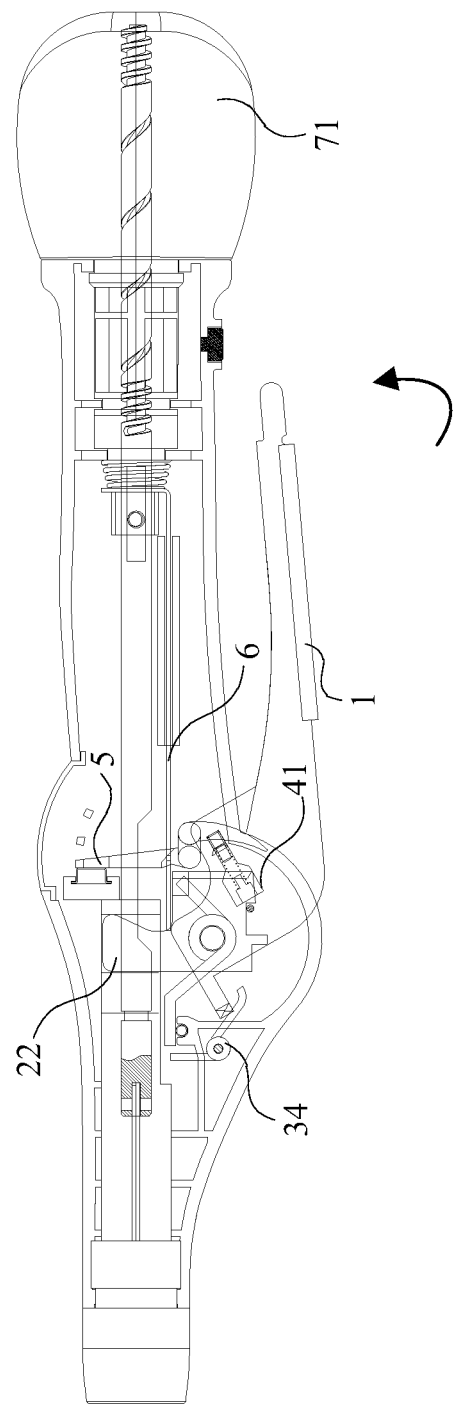
FIG. 9 is a schematic view of the handle assembly in the invalid firing state according to the first embodiment of the present disclosure.
Figure 10:
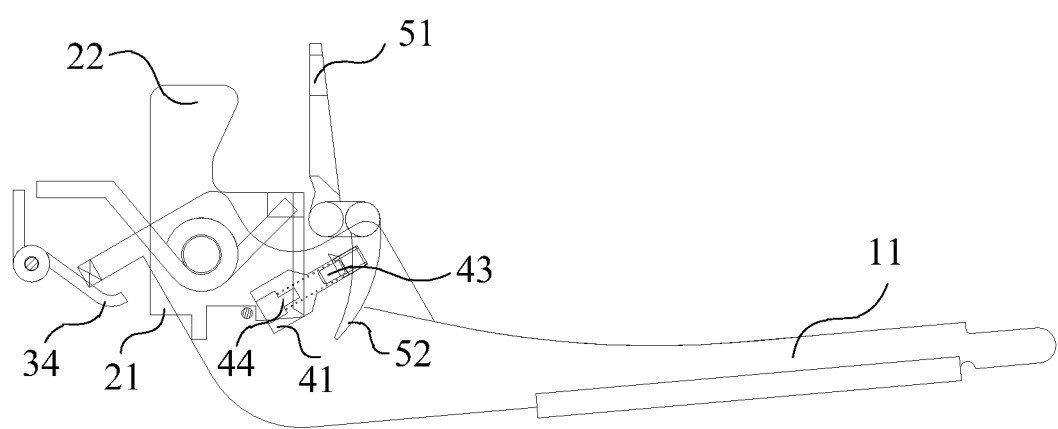
FIG. 10 is a schematic view of the handle assembly in the invalid firing state according to the first embodiment of the present disclosure.
Figure 11:
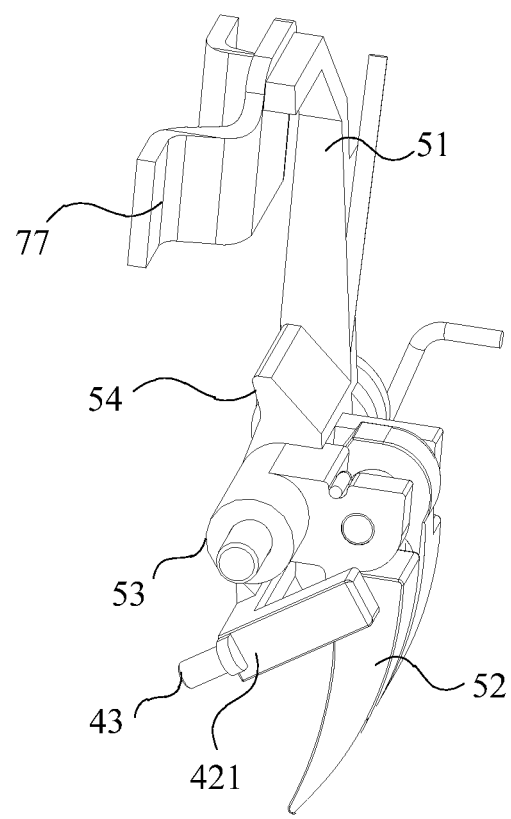
FIG. 11 is a schematic view of the handle assembly in the invalid firing state according to the first embodiment of the present disclosure.

FIGS. 9~11 show the structure of the handle assembly in an invalid firing state according to this embodiment. In this state, the pulling sheet 6 does not pull the indicator 5, so the position of the indicator 5 does not change, and the slider 42 is still located in the first section 411 of the first slot 41. The handle contact portion of the second handle 2 does not interfere with the slider 42, during the rotation path of the first handle 1. It should be noted that, in the initial position, the slider 42 is located at the end of the first section 411 of the first slot 41 away from the second section 412, which is the right end position shown in FIG. 9, under the action of the compression spring 45. Of course, the second end 52 of the indicator 5 may also limit the initial position of the slider 42. In this embodiment, the first end 11 of the first handle 1 is a grip portion, and the second end 12 includes a connecting portion; the first end 21 of the second handle 2 is located inside the cavity of the connecting portion, and the second end 22 is in contact with a staple pushing rod 75. At this time, the stapler is in an insurance state. Since the torsion force of the second torsion spring 34 is much smaller than a firing force, the first handle 1 can be rotated anticlockwise around the first pin 31 when the operator applies a small holding force, and the second handle 2 continues to enter inside the cavity of the first handle 1, that is, the first handle 1 and the second handle 2 are in an un-linked state, and the second handle 2 is not be rotated. When the operator compresses the first handle 1, the first handle 1 can be easily rotated, but the second handle 2 is not actuated to rotate, therefore the stapler cannot be fired. The operator can also get tactile feedback at this time, knowing that the first end 51 of the indicator 5 currently has not reached the second position area and the stapler has not been fired. When the external force is released, the first handle 1 will return by the action of the second torsion spring 34.

Figure 12:
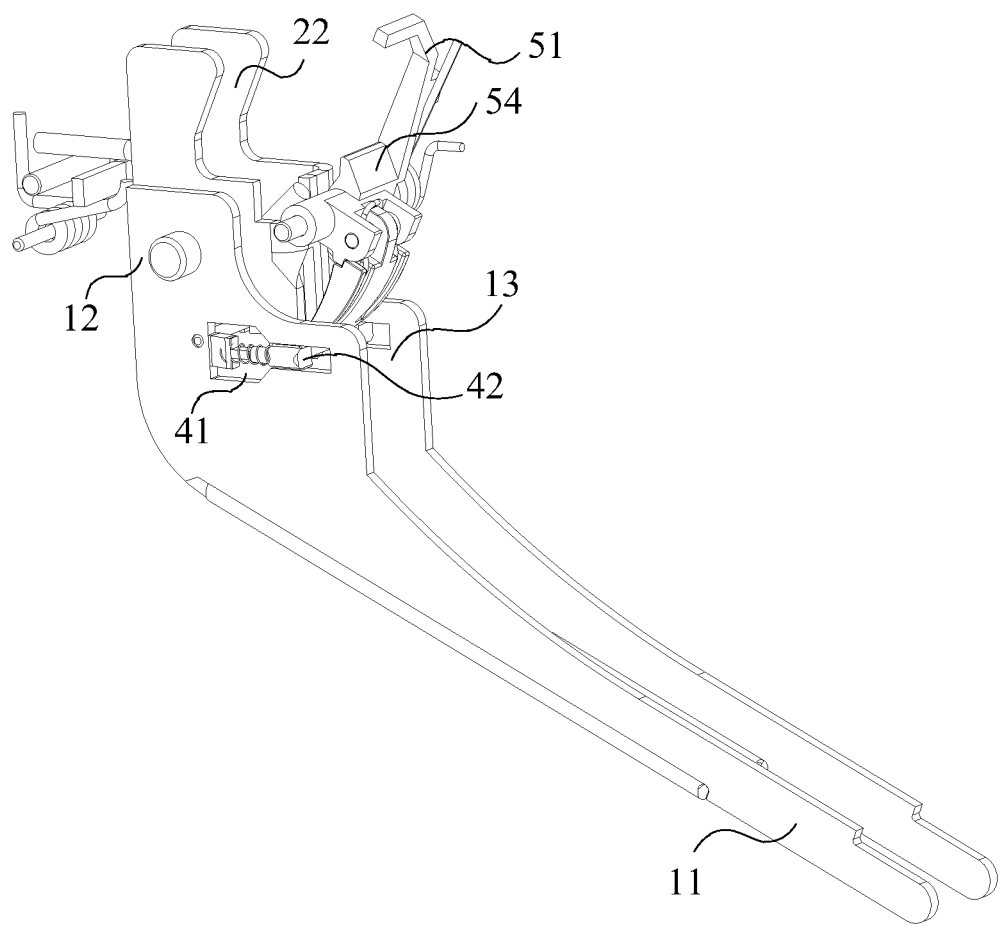
FIG. 12 is a schematic view of a handle assembly when the indicator moves to a second position area according to the first embodiment of the present disclosure.

FIG. 12 is a schematic view of the first end 51 of the indicator 5 moving to the second position area according to this embodiment. During this process, rotating the knob 71 causes the screw rod 76 to actuate the pulling sheet 6 to move toward the proximal end of the stapler, and to actuate the first end 51 of the indicator 5 to rotate clockwise, so that the first end 51 of the indicator 5 enters the second position area from the first position area. Therefore, the second end 52 of the indicator 5 pushes the slider 42 to move toward the second section 412 of the first slot 41, so that the first limiting structure 43 approaches the second limiting structure 44, and compressing the compression spring 45 to become deformed. At this time, during the rotation path of the first handle 1, the handle contact portion of the second handle 2 will interfere with the slider 42.

Figure 13:
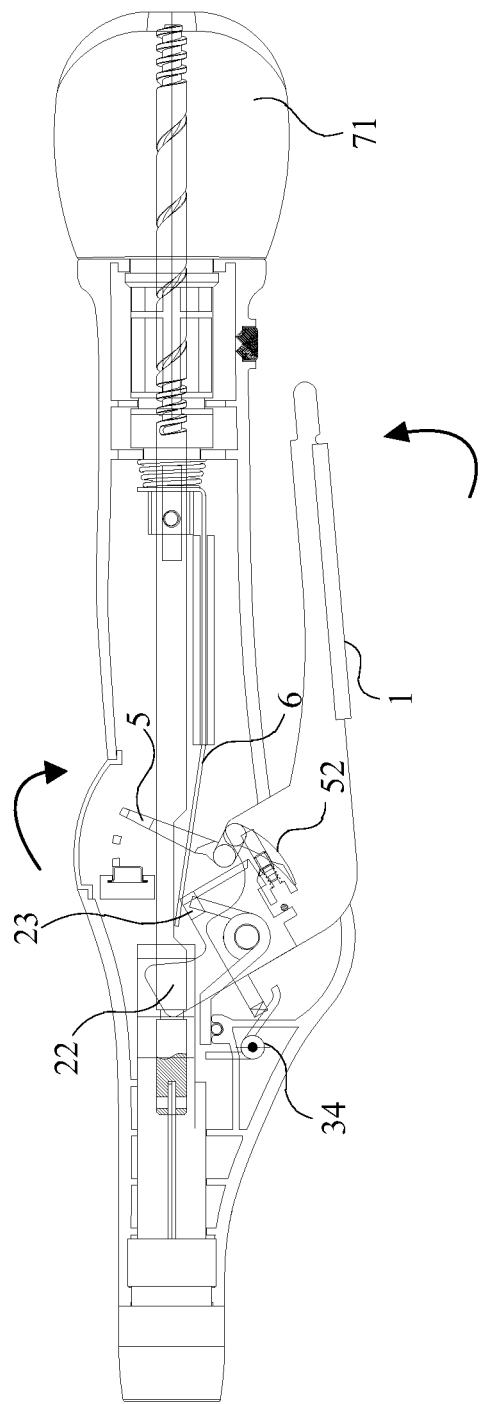
FIG. 13 is a schematic view of the handle assembly in a firing state according to the first embodiment of the present disclosure.
Figure 14:
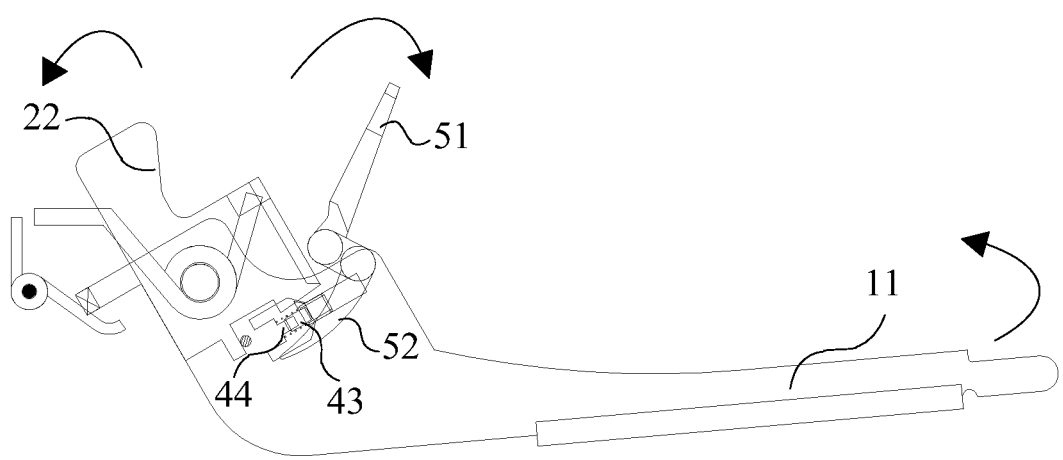
FIG. 14 is a schematic view of the handle assembly in a firing state according to the first embodiment of the present disclosure.
Figure 15:
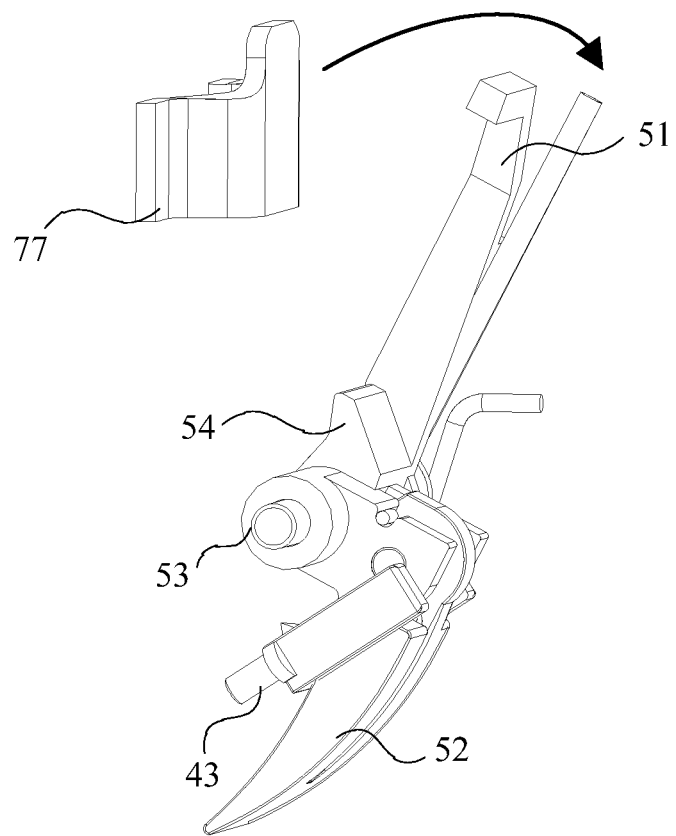
FIG. 15 is a schematic view of the handle assembly in a firing state according to the first embodiment of the present disclosure.
Figure 16:
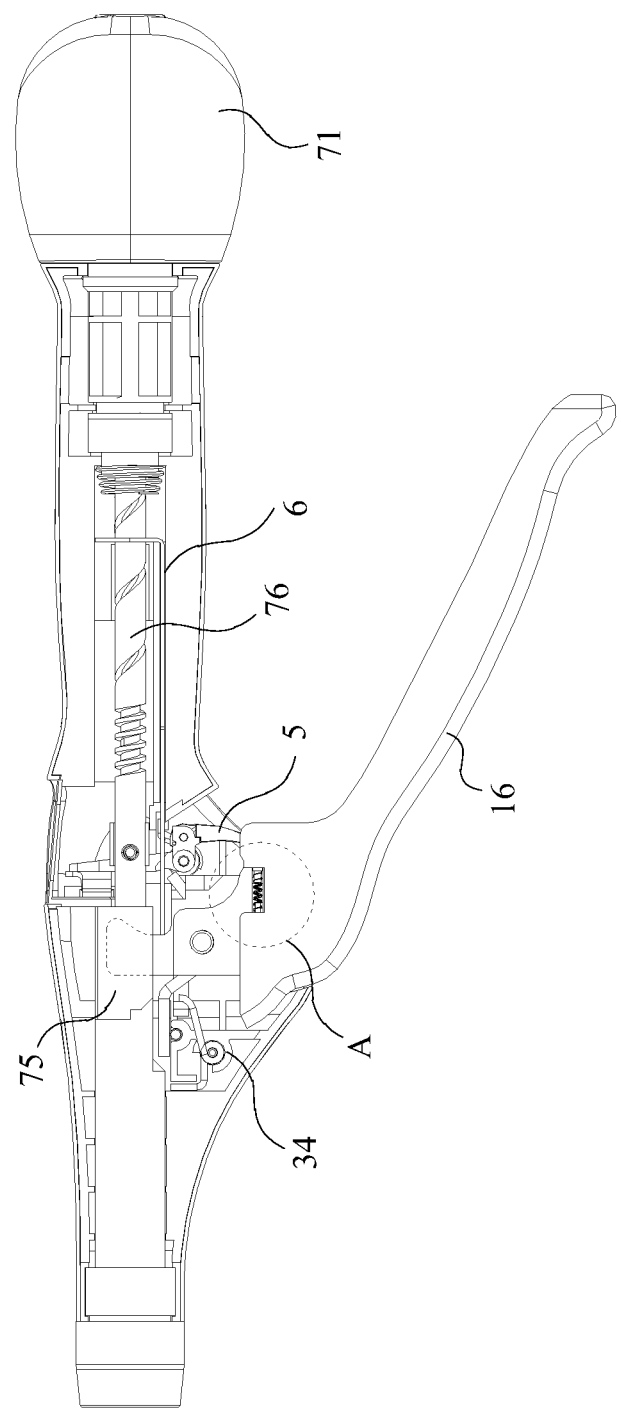
FIG. 16 is a schematic view of a handle assembly in an initial state according to a second embodiment of the present disclosure.
Figure 17:
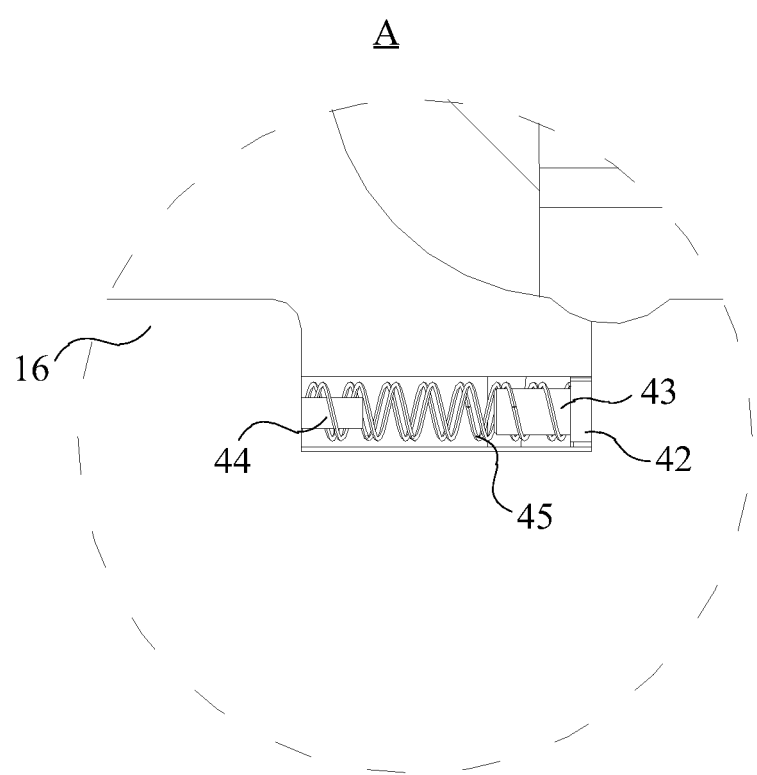
FIG. 17 is an enlarged view of area A in FIG. 16.

FIGS. 13~15 show the structure of the handle assembly of this embodiment when it is in a firing state. When the first handle 1 is compressed to rotate anticlockwise, the slider 42 is in contact with the handle contact portion of the second handle 2 and blocks the second handle 2 from continuing to enter the inner cavity of the first handle 1. As a result, the second handle 2 and the first handle 1 become linked. The second handle 2 rotates anticlockwise with the first handle 1, and the second end 22 of the second handle 2 pushes the staple pushing rod 75. The staple pushing rod 75 will further push a staple pushing sheet and a circular cutter of the stapler, thereby cutting and suturing the tissues to be operated.

As can be seen from FIG. 13, the compression spring 45 is gradually compressed during the movement of the slider 42. Further, the second handle 2 is also provided with a pulling sheet contacting portion 23. When the second handle 2 rotates from the insurance position to the firing position, the pulling sheet contacting portion 23 will jack the pulling sheet 6 up at an ejected vertex, so that the pulling hook of the pulling sheet 6 is separated from the indicator 5. At this time, the indicator 5 returns to the initial position in the anticlockwise direction. In this embodiment, a metal sheet 77 is provided at a position corresponding to the first end 51 of the indicator 5 in the casing 74 of the stapler. When the indicator 5 returns to the initial position, it will collide with the metal sheet 77 to make a sound, prompting the operator that the indicator has returned. Since the first end 51 of the indicator 5 returns to the first position area, the second end 52 of the indicator 5 is separated from the slider 42 after releasing the first handle 1. Then, after the indicator 5 returns, since the indicator 5 no longer exerts force on the slider 42, the deforming force of the compression spring 45 when restoring to the initial state can push the slider 42 to slide toward the first section 411 of the first slot 41 again, and return to the initial position. The second handle 2 also returns to the initial position under the restoring force of the first torsion spring 32. Since the first handle 1 is meshed with the second handle 2 under the action of the slider, it firstly returns with the second handle 2, and at the same time returns under the action of the second torsion spring 34.

FIGS. 16~24 show a schematic view of the structure of the stapler and the handle casing according to a second embodiment of the present disclosure. The difference between this embodiment and the first embodiment is that the first handle component includes a first handle 1 and a handle casing 16, the first handle 1 is provided with a first slot 41, and the handle casing 16 is provided with a second slot 161. Moreover, the first slot 41 on the first handle 1 is connected with the second slot 161 on the handle casing 16, and the second limiting structure 44 is located at the end of the second section of the second slot 161.

The first section of the second slot 161 corresponds to the first section 411 of the first slot 41, the second section of the second slot 161 corresponds to the second section 412 of the first slot 41, and the slider 42 passing through the first slot 41 is embedded in the second slot 161. The second handle 2 includes a handle contact portion; when the slider 42 is located in the first section of the second slot 161 and the first handle 1 is compressed to rotate in the first direction, the slider 42 is not in contact with the handle contact portion, the second handle 2 is in the insurance position, that is, although the first handle 1 rotates, it will not fire the stapler and the stapler is in the invalid firing state. Therefore, when the doctor presses the first handle 1 and the handle casing 16, the first handle 1 and the handle casing 16 can be easily rotated, but the second handle 2 will not be actuated. At the same time, since is the stapler in the invalid firing state, the holding force of the first handle 1 is very small. The doctor can also learn through this operation experience that the stapler is not fired, and the casing of the stapler is prevented from being cracked.

When the slider 42 is located in the second section of the second slot 161, and the first handle 1 and the handle casing 16 are rotated in the anticlockwise direction, the slider 42 is in contact with the handle contact portion and actuates the second handle 2 to rotate from the insurance position to the firing position. When the second handle 2 is rotated in the anticlockwise direction, it simultaneously pushes the staple pushing rod 75 to move toward the distal end of the stapler, thereby actuating the stapler to be fired.

It should be noted that the first section and the second section of the second slot 161 in the present disclosure are also relative concepts, not necessarily indicate the two ends of the second slot 161. That is say, in the perspective shown in FIG. 17, the first section of the second slot 161 is located on the right side of the second section. When the slider 42 is located in the first section of the second slot 161, it will not be in contact with the handle contact portion, and when the slider 42 is located in the second section of the second slot 161, it will be in contact with the handle contact portion.

In this embodiment, the movement of the slider 42 from the first section to the second section of the second slot 161 may also be controlled by the indicator 5. When the knob 71 is rotated in one direction, the screw rod 76 will move toward the proximal end of the stapler, actuating the pulling sheet 6 to move toward the proximal end of the stapler, and the pulling hook of the pulling sheet 6 may actuate the first end 51 of the indicator 5 to rotate in the second direction. Therefore, the second end 52 of the indicator 5 can push the slider 42 to move from the first section to the second section of the second slot 161, when the first end 51 of the indicator 5 moves from the first position area to the second position area.

In this embodiment, one end of the slider 42 is provided with a first limiting structure 43, and the end of the second section of the second slot 161 is provided with a second limiting structure 44. A compression spring 45 is located between the first limiting structure 43 and the second limiting structures 44. Herein, the end of the second section of the second slot 161 is the end of the second section away from the first section of the second slot 161, that is, the left position in FIG. 17. When the first end 51 of the indicator 5 moves from the first position area to the second position area, the second end 52 of the indicator 5 pushes the slider 42 to compress the compression spring 45 to become deformed. When the external force is released, the first end 51 of the indicator 5 can return to the first position area, therefore, the restoring force of the compression spring 45 can push the slider 42 to return to the first section of the second slot 161.

Further, in this embodiment, the first handle 1 includes a first cavity 13, two side walls of the first cavity 13 are respectively provided with two first slots 41, and the handle casing 16 is correspondingly provided with two second slots 161. The slider 42 includes two sliding portions 421 and a contact portion 422 between the sliding portions 421. The two sliding portions 421 are slidably located in the two second slots 161, respectively. The end portions of the second sections of the two second slot 161 are respectively provided with two second limiting structures 44. The ends of the two sliding portions are respectively provided with two first limiting structures 43, corresponding to the two second limiting structures 44. One compression spring 45 is located between each first limiting structure 43 and the corresponding second limiting structure 44. And, a length of the sliding portion 421 along an extension direction of the second slot 161 is greater than a length of the contact portion 422 along the extension direction of the second slot 161, to maintain the stability of the slider 42 in the first slot 41.

In this embodiment, by locating the compression spring 45 between the handle casing 16 and the slider 42, the working state of the compression spring 45 can be directly seen from the outside of the handle casing 16, which is convenient for inspection. The handle casing 16 does not need to be disassembled during installation and replacement, so that the installation and maintenance of the handle assembly and even the stapler are more cost-effective.

Figure 18:
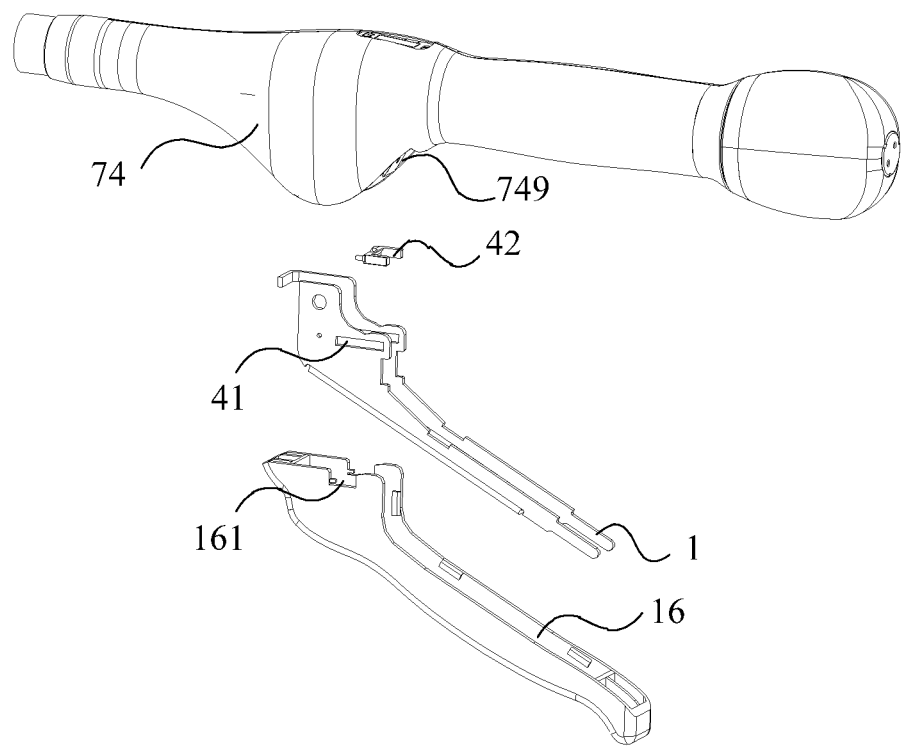
FIG. 18 is an explosion diagram of the handle assembly according to the second embodiment of the present disclosure.
Figure 19:
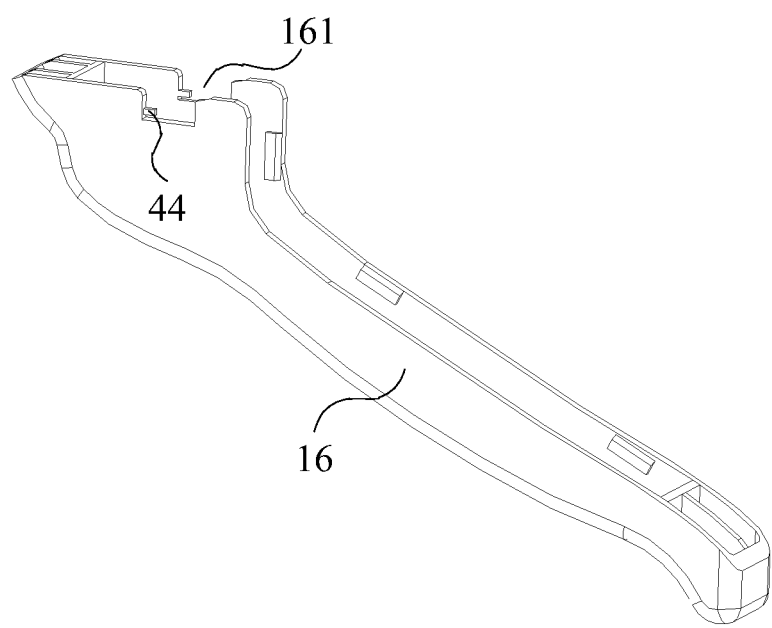
FIG. 19 is a stereoscopic view of the handle casing according to the second embodiment of the present disclosure.
Figure 20:
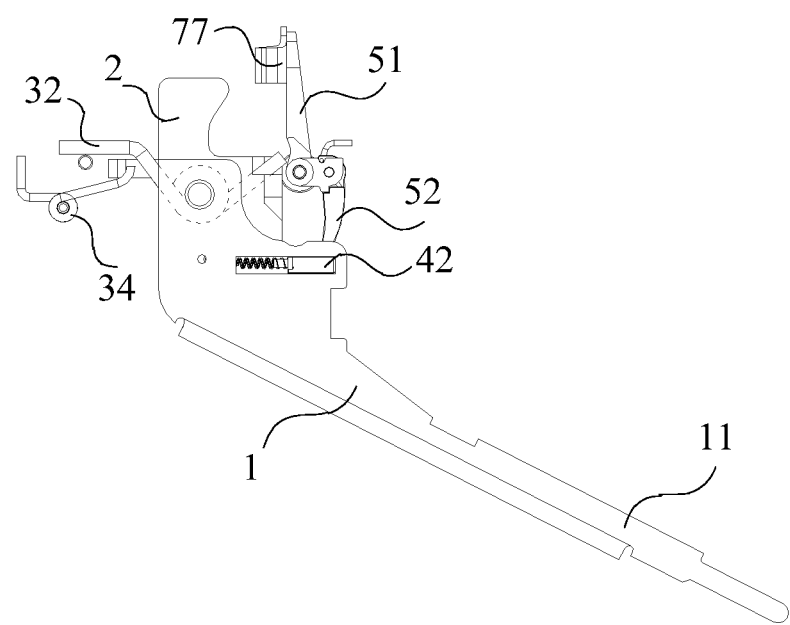
FIG. 20 is a front view of the handle assembly in the initial state according to the second embodiment of the present disclosure.

The structure of the handle casing 16 and the cooperation relationship with the stapler can be specifically referred to in FIGS. 18 and 19. The proximal end of the handle casing 16 is a grip portion, and the distal end is cooperated with the casing 74 of the stapler. The second slot 161 is opened at the distal end of the handle casing 16 and connected with an upper surface of the handle casing 16. Herein, the upper surface of the handle casing 16 is a top end surface of the handle casing 16 in the perspective of FIG. 5. That is, the second slot 161 is a slot with an upper opening, and the compression spring 45 can be directly installed and removed from an upper portion the handle casing 16. Due to the position-limiting effect of the two limiting structures, there is no need to worry about the position deviation of the compression spring 45 during normal use. One side of the distal end of the handle casing 16 is in contact with the casing 74 of the stapler. A position of casing 74 of the stapler corresponding to the other side of the distal end of the handle casing 16 is provided with a handle opening 749 to accommodate the handle casing 16 when being rotated anticlockwise.

In this embodiment, the first limiting structure 43 and the second limiting structure 44 are convex columns respectively. The two ends of the compression spring 45 are respectively sleeved on the first limiting structure 43 and the second limiting structure 44. Therefore, the sizes of the two convex columns are adapted to the size of the compression spring 45 to avoid the separation of the compression spring 45 from the convex columns. In practical application, the structure of the limiting structure of the compression spring 45 is not limited to this, and other structures are also within the protection scope of the present disclosure. For example, the first limiting structure 43 and the second limiting structure 44 can be hanging hooks respectively, and the two ends of the compression spring 45 are respectively hung on the first limiting structure 43 and the second limiting structure 44 to limit the compression spring 45.

Figure 21:
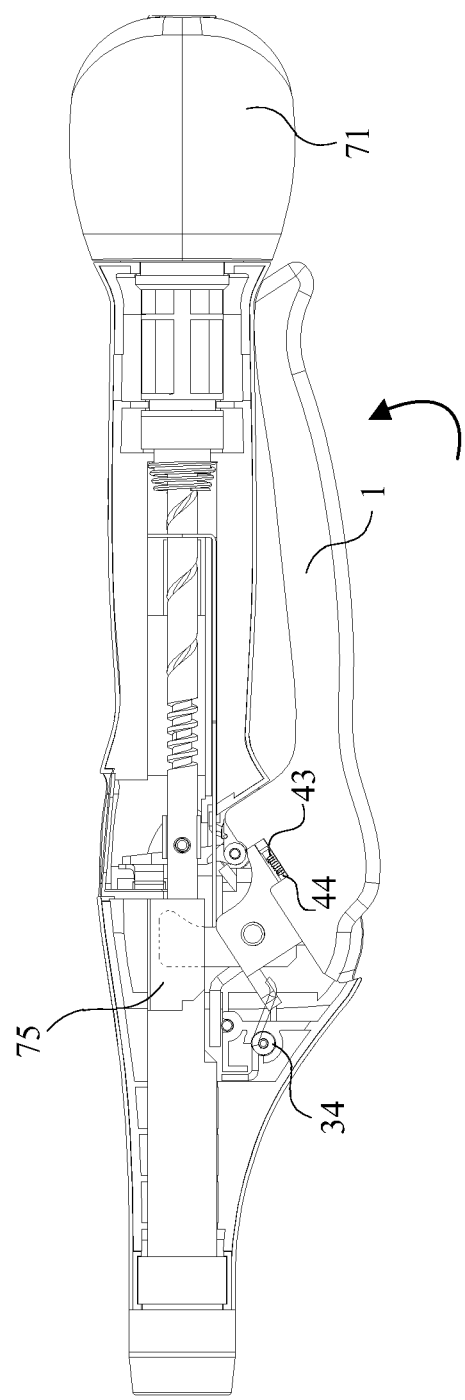
FIG. 21 is a schematic view of the handle assembly in invalid firing state according to the second embodiment of the present disclosure.
Figure 22:
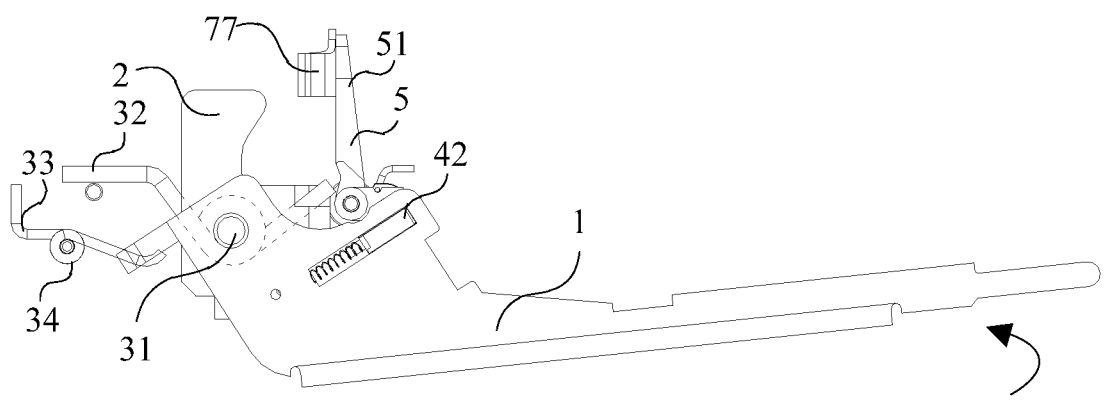
FIG. 22 is a schematic view of the handle assembly in invalid firing state according to the second embodiment of the present disclosure.

FIGS. 21 and 22 show the structure of the handle assembly in an invalid firing state according to this embodiment. In this state, the pulling sheet 6 does not pull the indicator 5, so the position of the indicator 5 does not change, and the slider 42 is still located in the first section of the second slot 161. The handle contact portion of the second handle 2 does not interfere with the slider 42, during the rotation path of the first handle 1. It should be noted that, in the initial position, the slider 42 is located at the end of the first section of the second slot 161 away from the second section, which is the right end position shown in the figure, under the action of the compression spring 45. Of course, the second end 52 of the indicator 5 may limit the initial position of the slider 42. At this time, the stapler is in the insurance state. Since the torsion force of the second torsion spring 34 is much smaller than the firing force, the first handle 1 can be rotated anticlockwise around the first pin 31 when the operator applies a small holding force, and the second handle 2 continues to enter inside the cavity of the first handle 1, that is, the first handle 1 and the second handle 2 are in an un-linked state, and the second handle 2 is not be rotated. When the operator compresses the first handle 1, the first handle 1 can be easily rotated, but the second handle 2 is not actuated to rotate, therefore the stapler cannot be fired. The operator can also get tactile feedback at this time, knowing that the first end 51 of the current indicator 5 has not reached the second position area and the stapler is not fired. When the external force is released, the first handle 1 will be returned by the action of the second torsion spring 34.

Figure 23:
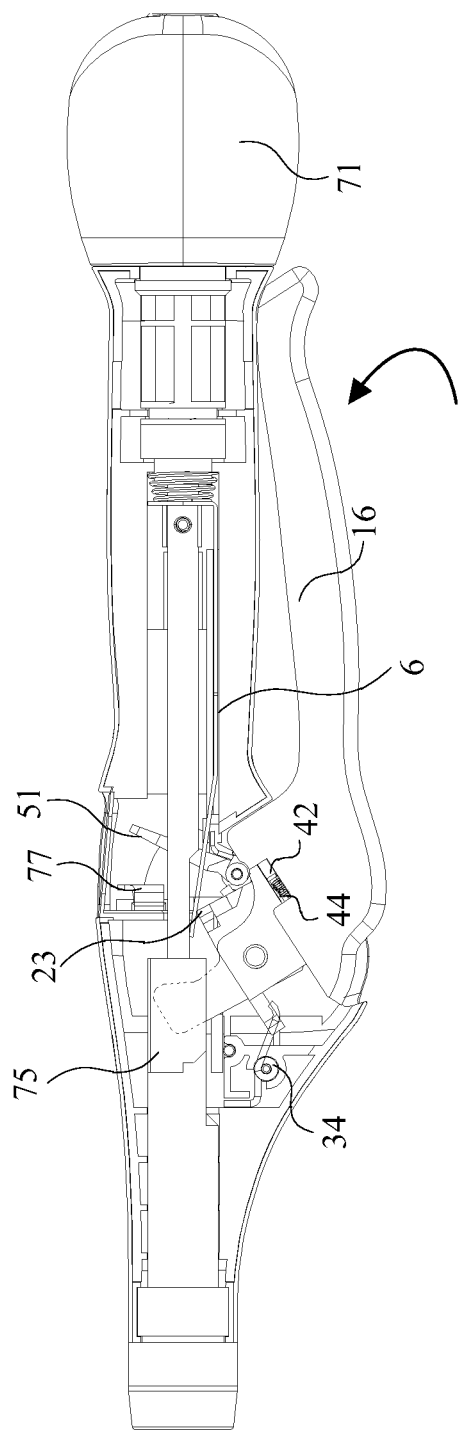
FIG. 23 is a schematic view of the handle assembly in a firing state according to the second embodiment of the present disclosure.
Figure 24:
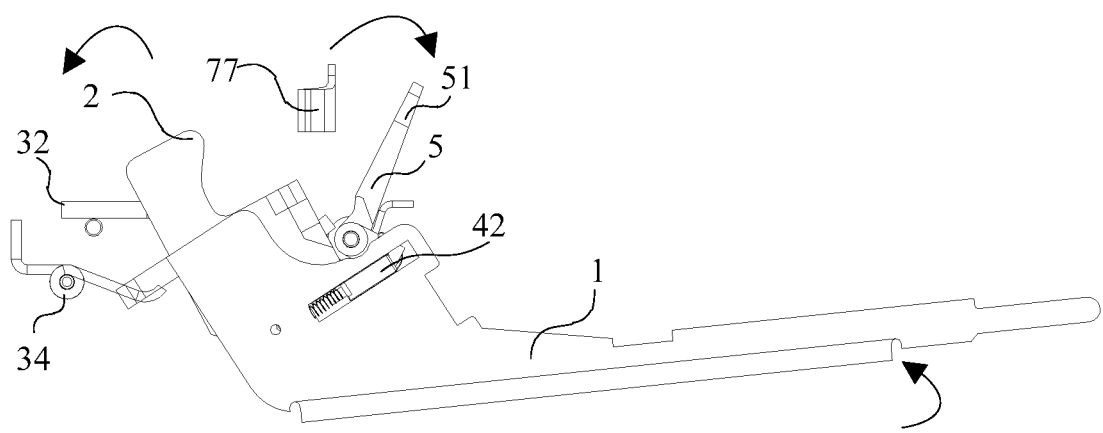
FIG. 24 is a schematic view of the handle assembly in a firing state according to the second embodiment of the present disclosure.

FIGS. 23 and 24 show the structure of the handle assembly in the firing state according to this embodiment. During this process, turning the knob 71 causes the screw rod 76 to actuate the pulling sheet 6 to move toward the proximal end of the stapler, and to actuate the first end 51 of the indicator 5 to rotate clockwise, so that the first end 51 of the indicator 5 enters the second position area from the first position area. Therefore, the second end 52 of the indicator 5 actuates the slider 42 to move toward the second section of the second slot 161, so that the first limiting structure 43 approaches the second limiting structure 44. When the first handle 1 is rotated anticlockwise, the slider 42 can be in contact with the handle contact portion 25 and blocks the second handle 2 from continuing to enter the inner cavity of the first handle 1. As a result, the second handle 2 and the first handle 1 become linked. The second handle 2 is rotated anticlockwise with the first handle 1, and the second end 22 of the second handle 2 pushes the staple pushing rod 75. The staple pushing rod 75 will further push a staple pushing sheet and a circular cutter of the stapler, thereby cutting and suturing the tissues to be operated.

As can be seen from the figure, the compression spring 45 is gradually compressed during the movement of the slider 42. When the stapler is fired, the pulling sheet contacting portion 23 will jack the pulling sheet 6 up at the ejected vertex, so that the pulling hook of the pulling sheet 6 is separated from the indicator 5. At this time, the indicator 5 returns to the initial position in the anticlockwise direction. In this embodiment, a metal sheet 77 is provided at a position corresponding to the first end 51 of the indicator 5 in the casing 74 of the stapler. When the indicator 5 returns to the initial position, it will collide with the metal sheet 77 to make a sound, prompting the operator that the indicator has returned. Since the first end 51 of the indicator 5 returns to the first position area, the second end 52 of the indicator 5 is separated from the slider 42 after releasing the first handle 1. Then, after the external force of the pointer 5 is released, the deforming force of the compression spring 45 when restoring to the initial state can push the slider 42 to slide toward the first end of the second slot 161 again, and return to the initial position. The second handle 2 also returns to the initial position under the restoring force of the first torsion spring 32. Since the first handle 1 is meshed with the second handle 2 under the action of the slider, it firstly returns with the second handle 2 and at the same time returns under the action of the second torsion spring 34.

The present disclosure further provides a stapler, including the handle assembly. When the stapler is not ready to be fired, the second handle cannot be actuated by the first handle, and the stapler won't be fired. The doctor can also judge whether the stapler is ready to be fired or not according to his operation experience. The second handle can only be actuated by the first handle when the stapler is ready to be fired, to fire the staple. Therefore, the stapler is prevented from being fired by mistake, and the casing of the stapler is prevented from being cracked at the same time. The stapler can control the linkage state of the first handle and the second handle by the moving position of the slider. After the firing is completed, the slider can return to the initial position by the return action of the compression spring.

The handle assembly and the stapler including the same has the following advantages.

In the present disclosure, the handle assembly includes the first handle component and the second handle, the linkage state of which can be controlled by the moving position of the slider and only the rotation of the second handle can fire the stapler, so as to avoid being fired by mistake when the stapler is not ready to be fired, and when in the invalid firing state, the first handle component can still be pressed and the casing of the stapler is prevented from being cracked; the compression spring is located between the slider and the slot, and the position of the compression spring is defined by a first limiting structure of the slider and a second limiting structure of the first handle component, therefore when the slider is free from the external force, the slider can be returned by the action of the compression spring.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. A handle assembly for firing a stapler, comprising:
a first handle component, provided with a slot comprising a first section and a second section connected with each other, in which slidably located a slider, wherein, one end of the slider is provided with a first limiting structure, one end portion of the second section of the slot is provided with a second limiting structure, and a compression spring is located between the first limiting structure and the second limiting structure;
a second handle, a first end of which is rotatably connected with the first handle component;
wherein, when the slider is in the first section of the slot, and the first handle component is rotated in a first direction, the slider is not in contact with the second handle, and the second handle is not rotated; when the slider is moved to the second section of the slot by external force and the first handle component is rotated in the first direction, the compression spring was deformed, and the slider is in contact with the second handle and actuates the second handle to rotate; when the slider is free from the external force, the restoring force of the compression spring actuates the slider to return.

2. The handle assembly according to claim 1, further comprising:
an indicator, movable between a first position area and a second position area;
wherein, when the indicator is moved from the first position area to the second position area, the slider is actuated to move from the first section to the second section of the slot.

3. The handle assembly according to claim 1, wherein, the slider comprises two sliding portions and a contact portion in between;
and the first handle component comprises an inner cavity, two side walls of which are respectively provided with one said slot; and the two sliding portions are located on the slots on the two side walls, respectively;
wherein, the end portion of the second section of each slot is provided with one second limiting structure; one end of each sliding portion is provided with one first limiting structure, corresponding to each second limiting structure; and one compression spring is provided between each first limiting structure and the corresponding second limiting structure.

4. The handle assembly according to claim 1, wherein, the first handle component comprises a first handle provided with the slot.

5. The handle assembly according to claim 1, wherein, the first handle component comprises a first handle and a handle casing sleeved on outside of the first handle, wherein, the slot comprises a first slot and a second slot connected with each other; the first slot comprises the first section and the second section, and the second slot comprises a first section and a second section corresponding to those of the first slot; the first slot is located on the first handle, and the second slot is located on the handle casing.

6. The handle assembly according to claim 5, wherein, one end of the slider is embedded in the second slot, and the second limiting structure is located at the end portion of the second section of the second slot.

7. The handle assembly according to claim 6, wherein, two sides of the first handle are respectively provided with two first slots, and the handle casing is correspondingly provided with two second slots, and the slider comprises two sliding portions at two ends thereof and a contact portion in between; and each sliding portion is embedded in the corresponding second slot respectively;
wherein, the end portion of the second section of each second slot is provided with one second limiting structure, and one end of each sliding portion is provided with one first limiting structure, one compression spring is provided between each first limiting structure and the corresponding second limiting structure.

8. The handle assembly according to claim 3, wherein, a length of the sliding portion along an extension direction of the slot is greater than a length of the contact portion along the extension direction of the slot.

9. The handle assembly according to claim 5, wherein, a distal end of the handle casing is provided with the second slot which is connected with an upper surface of the handle casing.

10. The handle assembly according to claim 5, wherein, a first side of a distal end of the handle casing is in contact with a casing of the stapler, and the casing of the stapler is provided with a handle opening at a position corresponding to a second side of the distal end of the handle casing, for accommodating the distal end of the handle casing when being rotated in the first direction.

11. The handle assembly according to claim 1, wherein, the first limiting structure and the second limiting structure are convex columns, respectively, and two ends of the compression spring are respectively sleeved on the first limiting structure and the second limiting structure.

12. The handle assembly according to claim 11, wherein, a height of the second section of the slot is greater than that of the first section of the slot, and a smooth transition is made between the first section and the second section; an inner wall of the second section is provided with a support seat for a convex column; on which the second limiting structure is located, and a height of the support seat is greater than that of the second limiting structure.

13. The handle assembly according to claim 1, wherein, the first limiting structure and the second limiting structure are hanging hooks, respectively, and two ends of the compression spring are respectively hung on the first limiting structure and the second limiting structure.

14. The handle assembly according to claim 1, further comprising:
 a first pin, passing through the first handle component and the second handle, and fixed to a casing of the stapler;
 a first torsion spring, sleeved on the first pin, and two ends of the first torsion spring being respectively in contact with the casing of the stapler and the second handle;
 a second pin, fixed to the casing of the stapler;
 a second torsion spring, sleeved on the second pin, and two ends of the second torsion spring being respectively in contact with the casing of the stapler and the first handle component.

15. The handle assembly according to claim 1, further comprising:
 a first pin, passing through the first handle component and the second handle, and fixed to a casing of the stapler;
 a first torsion spring, sleeved on the first pin, and two ends of the first torsion spring being respectively in contact with the casing of the stapler and the second handle;
 a compression spring, located between the first handle component and the casing of the stapler.

16. The handle assembly according to claim 1, further comprising:
 a first pin, passing through the first handle component and fixed to the second handle;
 a first torsion spring, sleeved on the first pin, and the two ends of the first torsion spring being respectively in contact with the first handle component and the second handle;
 a second pin, passing through the second handle and fixed to a casing of the stapler;
 a second torsion spring, sleeved on the second pin, and two ends of the second torsion spring being respectively in contact with the second handle and the casing of the stapler.

17. The handle assembly according to claim 2, wherein, the indicator is connected to a distal end of a pulling sheet; a proximal end of the pulling sheet is sleeved on a screw rod having a distal end connected to a knob; when the knob is rotated to pull the pulling sheet to move toward a proximal end of the stapler, the indicator is moved by the pulling sheet from the first position area to the second position area.

18. A stapler, comprising the handle assembly according to claim 1.

19. The handle assembly according to claim 7, wherein, a length of the sliding portion along an extension direction of the slot is greater than a length of the contact portion along the extension direction of the slot.

* * * * *